(12) United States Patent
Churchill et al.

(10) Patent No.: US 10,779,877 B2
(45) Date of Patent: *Sep. 22, 2020

(54) POWER MODULATED ENDOMETRIAL LINING TISSUE ABLATION

(71) Applicant: HOLOGIC, INC., Marlborough, MA (US)

(72) Inventors: William Lucas Churchill, Bolton, MA (US); Danielle Gline Allen, Derry, NH (US)

(73) Assignee: Hologic, Inc., Marlborough, MA (US)

( * ) Notice: Subject to any disclaimer, the term of this patent is extended or adjusted under 35 U.S.C. 154(b) by 94 days.

This patent is subject to a terminal disclaimer.

(21) Appl. No.: 16/001,366

(22) Filed: Jun. 6, 2018

(65) Prior Publication Data

US 2018/0280072 A1 Oct. 4, 2018

Related U.S. Application Data

(63) Continuation of application No. 14/574,070, filed on Dec. 17, 2014, now Pat. No. 10,004,553.

(60) Provisional application No. 61/920,152, filed on Dec. 23, 2013.

(51) Int. Cl.
*A61B 18/12* (2006.01)
*A61B 18/14* (2006.01)
*A61B 18/00* (2006.01)

(52) U.S. Cl.
CPC .. *A61B 18/1233* (2013.01); *A61B 2018/0072* (2013.01); *A61B 2018/00267* (2013.01); *A61B 2018/00559* (2013.01); *A61B 2018/00577* (2013.01); *A61B 2018/00642* (2013.01); *A61B 2018/00702* (2013.01); *A61B 2018/00875* (2013.01); *A61B 2018/126* (2013.01); *A61B 2018/1475* (2013.01)

(58) Field of Classification Search
CPC ...... A61B 18/1233; A61B 2018/00875; A61B 2018/00559
See application file for complete search history.

(56) References Cited

U.S. PATENT DOCUMENTS

| | | | |
|---|---|---|---|
| 4,474,179 A | 10/1984 | Koch | |
| 5,817,093 A | 1/1998 | Williamson, IV et al. | |
| 5,769,880 A | 6/1998 | Truckai et al. | |
| 5,954,717 A | 9/1999 | Behl et al. | |
| 6,033,399 A | 3/2000 | Gines | |
| 6,080,149 A | 6/2000 | Huang et al. | |

(Continued)

OTHER PUBLICATIONS

PCT International Search Report and Written Opinion for International Application No. PCT/US2014/070959, Applicant Hologic, Inc., forms PCT/ISA/210, 220, and 237, dated Mar. 24, 2015 (16 pages).

*Primary Examiner* — Jaymi E Della
*Assistant Examiner* — Sean W Collins
(74) *Attorney, Agent, or Firm* — Vista IP Law Group, LLP

(57) ABSTRACT

A system is configured to delivering radiofrequency power to the endometrial lining tissue of a uterine cavity, including modulating the delivered power so that a measured impedance of the endometrial lining tissue tracks a target impedance as a function of time, wherein the target tissue impedance is derived from a function that approximates a preferred endometrial lining tissue ablation impedance curve that is determined based upon a measured impedance of the endometrial lining tissue after RF power has been delivered for a predetermined initial time period.

16 Claims, 9 Drawing Sheets

(56) References Cited

U.S. PATENT DOCUMENTS

| | | | |
|---|---|---|---|
| 6,508,815 | B1 | 1/2003 | Strul et al. |
| 6,843,789 | B2 | 1/2005 | Goble |
| 8,080,008 | B2 | 12/2011 | Wham et al. |
| 8,152,801 | B2 | 4/2012 | Goldberg et al. |
| 8,241,275 | B2 | 4/2012 | Hong et al. |
| 8,357,151 | B2 | 1/2013 | Goldberg et al. |
| 8,486,060 | B2 | 7/2013 | Kotmel et al. |
| 9,333,034 | B2 | 5/2016 | Hancock |
| 2005/0203504 | A1 | 9/2005 | Wham et al. |
| 2007/0173804 | A1 | 7/2007 | Wham et al. |
| 2007/0282320 | A1 | 12/2007 | Buysse et al. |
| 2008/0071257 | A1 | 3/2008 | Kotmel et al. |
| 2008/0228181 | A1 | 9/2008 | Godara et al. |
| 2009/0234351 | A1 | 9/2009 | Desinger et al. |
| 2010/0324548 | A1 | 12/2010 | Godara et al. |
| 2011/0144635 | A1 | 6/2011 | Harper et al. |
| 2012/0136354 | A1 | 3/2012 | Rupp |
| 2013/0304060 | A1 | 11/2013 | Truckai et al. |
| 2015/0224326 | A1 | 8/2015 | Toth et al. |

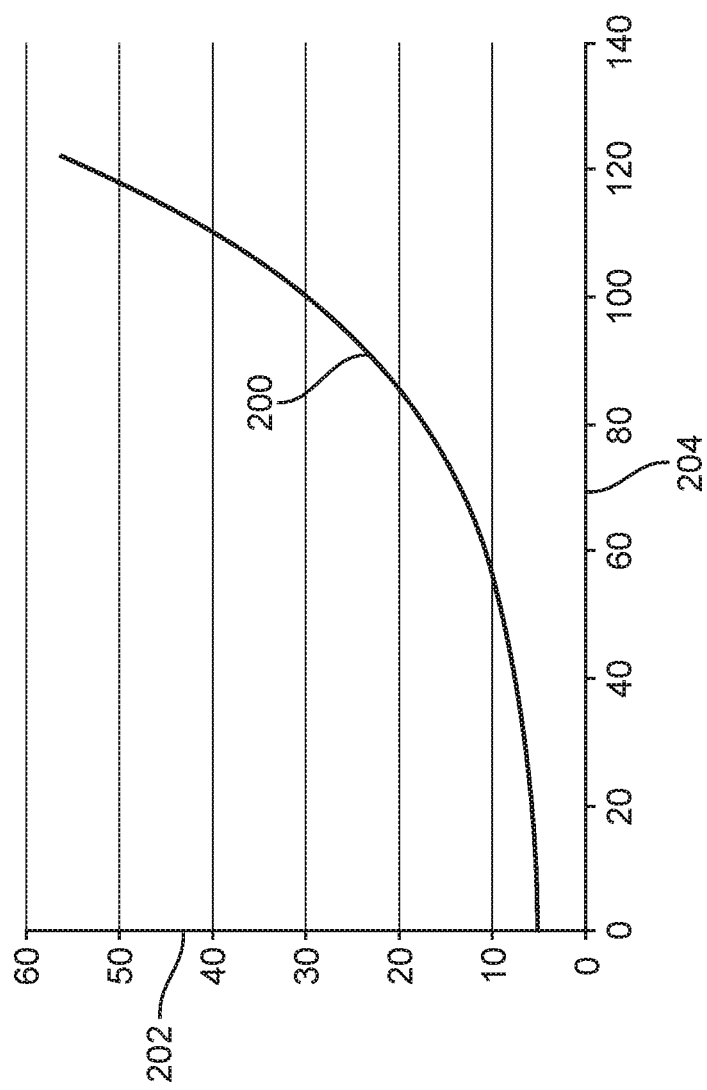

| 302 | 304 | 302 | 304 | 302 | 304 |
|---|---|---|---|---|---|
| 5 | 1 | 8 | 41 | 18 | 81 |
| 5 | 2 | 8 | 42 | 18 | 82 |
| 5 | 3 | 8 | 43 | 19 | 83 |
| 5 | 4 | 8 | 44 | 19 | 84 |
| 5 | 5 | 8 | 45 | 20 | 85 |
| 5 | 6 | 8 | 46 | 20 | 86 |
| 5 | 7 | 9 | 47 | 21 | 87 |
| 5 | 8 | 9 | 48 | 21 | 88 |
| 5 | 9 | 9 | 49 | 22 | 89 |
| 5 | 10 | 9 | 50 | 23 | 90 |
| 5 | 11 | 9 | 51 | 23 | 91 |
| 5 | 12 | 9 | 52 | 24 | 92 |
| 6 | 13 | 10 | 53 | 24 | 93 |
| 6 | 14 | 10 | 54 | 25 | 94 |
| 6 | 15 | 10 | 55 | 26 | 95 |
| 6 | 16 | 10 | 56 | 26 | 96 |
| 6 | 17 | 10 | 57 | 27 | 97 |
| 6 | 18 | 11 | 58 | 28 | 98 |
| 6 | 19 | 11 | 59 | 29 | 99 |
| 6 | 20 | 11 | 60 | 30 | 100 |
| 6 | 21 | 11 | 61 | 30 | 101 |
| 6 | 22 | 11 | 62 | 31 | 102 |
| 6 | 23 | 12 | 63 | 32 | 103 |
| 6 | 24 | 12 | 64 | 33 | 104 |
| 6 | 25 | 12 | 65 | 34 | 105 |
| 6 | 26 | 13 | 66 | 35 | 106 |
| 6 | 27 | 13 | 67 | 36 | 107 |
| 6 | 28 | 13 | 68 | 37 | 108 |
| 7 | 29 | 13 | 69 | 38 | 109 |
| 7 | 30 | 14 | 70 | 39 | 110 |
| 7 | 31 | 14 | 71 | 41 | 111 |
| 7 | 32 | 14 | 72 | 42 | 112 |
| 7 | 33 | 15 | 73 | 43 | 113 |
| 7 | 34 | 15 | 74 | 44 | 114 |
| 7 | 35 | 15 | 75 | 46 | 115 |
| 7 | 36 | 16 | 76 | 47 | 116 |
| 7 | 37 | 16 | 77 | 48 | 117 |
| 7 | 38 | 17 | 78 | 50 | 118 |
| 8 | 39 | 17 | 79 | 51 | 119 |
| 8 | 40 | 17 | 80 | 53 | 120 |
|  |  |  |  | 55 | 121 |
|  |  |  |  | 56 | 122 |

| 302 | 304 | 502 | | | |
|---|---|---|---|---|---|
| 5 | 1 | | | | |
| 5 | 2 | | | | |
| 5 | 3 | | | | |
| 5 | 4 | | | | |
| 5 | 5 | 10 | 10 | 0.89238 | |
| 5 | 6 | 10.03459 | | | |
| 5 | 7 | 10.07033 | | | |
| 5 | 8 | 10.10724 | | | |
| 5 | 9 | 10.14537 | | | |
| 5 | 10 | 10.18476 | | | |
| 5 | 11 | 10.22544 | | | |
| 5 | 12 | 10.26747 | | | |
| 6 | 13 | 10.31088 | | | |
| 6 | 14 | 10.35572 | | | |
| 6 | 15 | 10.40204 | | | |
| 6 | 16 | 10.44989 | | | |
| 6 | 17 | 10.49932 | | | |
| 6 | 18 | 10.55037 | | | |
| 6 | 19 | 10.60311 | | | |
| 6 | 20 | 10.65758 | | | |
| 6 | 21 | 10.71385 | | | |
| 6 | 22 | 10.77198 | | | |
| 6 | 23 | 10.83202 | | | |
| 6 | 24 | 10.89404 | | | |
| 6 | 25 | 10.9581 | | | |
| 6 | 26 | 11.02428 | | | |
| 6 | 27 | 11.09264 | | | |
| 6 | 28 | 11.16325 | | | |
| 7 | 29 | 11.23619 | | | |
| 7 | 30 | 11.31153 | | | |
| 7 | 31 | 11.38936 | | | |
| 7 | 32 | 11.46975 | | | |
| 7 | 33 | 11.5528 | | | |
| 7 | 34 | 11.63858 | | | |
| 7 | 35 | 11.72719 | | | |
| 7 | 36 | 11.81871 | | | |
| 7 | 37 | 11.91326 | | | |
| 7 | 38 | 12.01092 | | | |
| 8 | 39 | 12.1118 | | | |
| 8 | 40 | 12.21601 | | | |
| 8 | 41 | 12.32365 | | | |
| 8 | 42 | 12.43484 | | | |
| 8 | 43 | 12.5497 | | | |
| 8 | 44 | 12.66834 | | | |
| 8 | 45 | 12.79089 | | | |
| 8 | 46 | 12.91748 | | | |
| 9 | 47 | 13.04825 | | | |
| 9 | 48 | 13.18332 | | | |
| 9 | 49 | 13.32285 | | | |
| 9 | 50 | 13.46698 | | | |
| 9 | 51 | 13.61586 | | | |
| 9 | 52 | 13.76964 | | | |
| 10 | 53 | 13.9285 | | | |

| 302 | 304 | 502 |
|---|---|---|
| 10 | 54 | 14.09259 |
| 10 | 55 | 14.26209 |
| 10 | 56 | 14.43718 |
| 10 | 57 | 14.61804 |
| 11 | 58 | 14.80486 |
| 11 | 59 | 14.99784 |
| 11 | 60 | 15.19718 |
| 11 | 61 | 15.40309 |
| 11 | 62 | 15.61579 |
| 12 | 63 | 15.8355 |
| 12 | 64 | 16.06245 |
| 12 | 65 | 16.29689 |
| 13 | 66 | 16.53905 |
| 13 | 67 | 16.78919 |
| 13 | 68 | 17.04758 |
| 13 | 69 | 17.31449 |
| 14 | 70 | 17.5902 |
| 14 | 71 | 17.87499 |
| 14 | 72 | 18.16917 |
| 15 | 73 | 18.47305 |
| 15 | 74 | 18.78695 |
| 15 | 75 | 19.11119 |
| 16 | 76 | 19.44612 |
| 16 | 77 | 19.79209 |
| 17 | 78 | 20.14947 |
| 17 | 79 | 20.51862 |
| 17 | 80 | 20.89995 |
| 18 | 81 | 21.29384 |
| 18 | 82 | 21.70072 |
| 19 | 83 | 22.12101 |
| 19 | 84 | 22.55516 |
| 20 | 85 | 23.00362 |
| 20 | 86 | 23.46686 |
| 21 | 87 | 23.94536 |
| 21 | 88 | 24.43965 |
| 22 | 89 | 24.95022 |
| 23 | 90 | 25.47763 |
| 23 | 91 | 26.02242 |
| 24 | 92 | 26.58517 |
| 24 | 93 | 27.16647 |
| 25 | 94 | 27.76693 |
| 26 | 95 | 28.38718 |
| 26 | 96 | 29.02788 |
| 27 | 97 | 29.6897 |
| 28 | 98 | 30.37334 |
| 29 | 99 | 31.07951 |
| 30 | 100 | 31.80896 |
| 30 | 101 | 32.56245 |
| 31 | 102 | 33.34078 |
| 32 | 103 | 34.14477 |
| 33 | 104 | 34.97526 |
| 34 | 105 | 35.83313 |
| 35 | 106 | 36.71927 |

| 302 | 304 | 502 |
|---|---|---|
| 36 | 107 | 37.63463 |
| 37 | 108 | 38.58015 |
| 38 | 109 | 39.55685 |
| 39 | 110 | 40.56574 |
| 41 | 111 | 41.60789 |
| 42 | 112 | 42.68439 |
| 43 | 113 | 43.79638 |
| 44 | 114 | 44.94502 |
| 46 | 115 | 46.13152 |
| 47 | 116 | 47.35714 |
| 48 | 117 | 48.62315 |
| 50 | 118 | 49.9309 |
| 51 | 119 | 51.28176 |
| 53 | 120 | 52.67714 |
| 55 | 121 | 54.11852 |
| 56 | 122 | 55.60742 |

| 302 | 304 | 702 | | |
|---|---|---|---|---|
| 5 | 1 | | | |
| 5 | 2 | | | |
| 5 | 3 | | | |
| 5 | 4 | | 2 | 1.070856 |
| 5 | 5 | 2 | | |
| 5 | 6 | 2.041513 | | |
| 5 | 7 | 2.084395 | | |
| 5 | 8 | 2.128691 | | |
| 5 | 9 | 2.174446 | | |
| 5 | 10 | 2.22171 | | |
| 5 | 11 | 2.270532 | | |
| 5 | 12 | 2.320963 | | |
| 6 | 13 | 2.373057 | | |
| 6 | 14 | 2.426867 | | |
| 6 | 15 | 2.482452 | | |
| 6 | 16 | 2.539869 | | |
| 6 | 17 | 2.599178 | | |
| 6 | 18 | 2.660442 | | |
| 6 | 19 | 2.723726 | | |
| 6 | 20 | 2.789096 | | |
| 6 | 21 | 2.856621 | | |
| 6 | 22 | 2.926372 | | |
| 6 | 23 | 2.998422 | | |
| 6 | 24 | 3.072847 | | |
| 6 | 25 | 3.149725 | | |
| 6 | 26 | 3.229137 | | |
| 6 | 27 | 3.311167 | | |
| 6 | 28 | 3.395902 | | |
| 7 | 29 | 3.483429 | | |
| 7 | 30 | 3.573841 | | |
| 7 | 31 | 3.667234 | | |
| 7 | 32 | 3.763705 | | |
| 7 | 33 | 3.863357 | | |
| 7 | 34 | 3.966293 | | |
| 7 | 35 | 4.072622 | | |
| 7 | 36 | 4.182456 | | |
| 7 | 37 | 4.295911 | | |
| 7 | 38 | 4.413106 | | |
| 8 | 39 | 4.534164 | | |
| 8 | 40 | 4.659212 | | |
| 8 | 41 | 4.788382 | | |
| 8 | 42 | 4.921811 | | |
| 8 | 43 | 5.059637 | | |
| 8 | 44 | 5.202007 | | |
| 8 | 45 | 5.34907 | | |
| 8 | 46 | 5.50098 | | |
| 9 | 47 | 5.657898 | | |
| 9 | 48 | 5.819989 | | |
| 9 | 49 | 5.987422 | | |
| 9 | 50 | 6.160375 | | |
| 9 | 51 | 6.339029 | | |
| 9 | 52 | 6.523572 | | |
| 10 | 53 | 6.714198 | | |

| 302 | 304 | 702 |
|---|---|---|
| 10 | 54 | 6.911108 |
| 10 | 55 | 7.114509 |
| 10 | 56 | 7.324614 |
| 10 | 57 | 7.541645 |
| 11 | 58 | 7.765831 |
| 11 | 59 | 7.997406 |
| 11 | 60 | 8.236615 |
| 11 | 61 | 8.483709 |
| 11 | 62 | 8.738948 |
| 12 | 63 | 9.0026 |
| 12 | 64 | 9.274944 |
| 12 | 65 | 9.556265 |
| 13 | 66 | 9.846859 |
| 13 | 67 | 10.14703 |
| 13 | 68 | 10.4571 |
| 13 | 69 | 10.77739 |
| 14 | 70 | 11.10824 |
| 14 | 71 | 11.44999 |
| 14 | 72 | 11.80301 |
| 15 | 73 | 12.16766 |
| 15 | 74 | 12.54434 |
| 15 | 75 | 12.93343 |
| 16 | 76 | 13.33535 |
| 16 | 77 | 13.75051 |
| 17 | 78 | 14.17936 |
| 17 | 79 | 14.62235 |
| 17 | 80 | 15.07994 |
| 18 | 81 | 15.55261 |
| 18 | 82 | 16.04087 |
| 19 | 83 | 16.54522 |
| 19 | 84 | 17.06619 |
| 20 | 85 | 17.60434 |
| 20 | 86 | 18.16023 |
| 21 | 87 | 18.73444 |
| 21 | 88 | 19.32758 |
| 22 | 89 | 19.94027 |
| 23 | 90 | 20.57315 |
| 23 | 91 | 21.2269 |
| 24 | 92 | 21.9022 |
| 24 | 93 | 22.59976 |
| 25 | 94 | 23.32031 |
| 26 | 95 | 24.06462 |
| 26 | 96 | 24.83346 |
| 27 | 97 | 25.62764 |
| 28 | 98 | 26.44801 |
| 29 | 99 | 27.29541 |
| 30 | 100 | 28.17075 |
| 30 | 101 | 29.07494 |
| 31 | 102 | 30.00894 |
| 32 | 103 | 30.97373 |
| 33 | 104 | 31.97031 |
| 34 | 105 | 32.99975 |
| 35 | 106 | 34.06313 |

| 302 | 304 | 702 |
|---|---|---|
| 36 | 107 | 35.16155 |
| 37 | 108 | 36.29619 |
| 38 | 109 | 37.46822 |
| 39 | 110 | 38.67889 |
| 41 | 111 | 39.92947 |
| 42 | 112 | 41.22127 |
| 43 | 113 | 42.55565 |
| 44 | 114 | 43.93402 |
| 46 | 115 | 45.35782 |
| 47 | 116 | 46.82856 |
| 48 | 117 | 48.34778 |
| 50 | 118 | 49.91708 |
| 51 | 119 | 51.53811 |
| 53 | 120 | 53.21257 |
| 55 | 121 | 54.94223 |
| 56 | 122 | 56.7289 |

FIG. 7

POWER MODULATED ENDOMETRIAL LINING TISSUE ABLATION

RELATED APPLICATION DATA

The present application is a continuation of pending U.S. patent application Ser. No. 14/574,070, filed Dec. 17, 2014, which claims the benefit under 35 U.S.C. § 119 to U.S. provisional patent application Ser. No. 61/920,152, filed Dec. 23, 2013. The foregoing applications are each hereby incorporated by reference into the present application in their entirety.

FIELD OF INVENTION

The disclosed inventions pertain generally to systems and methods for thermally treating the interior surfaces of body organs. More specifically, the disclosed inventions pertain to a system and method for ablating the endometrial lining tissue of the uterus.

BACKGROUND

Thermal ablation or coagulation of the interior lining of a body organ is a procedure which involves heating the organ lining to a temperature that destroys the cells of the lining tissue. Such a procedure may be performed as a treatment to one of many conditions, such as menorrhagia, which is characterizes by chronic bleeding of the endometrial tissue layer of the uterus. Existing methods for effecting thermal ablation of the endometrial lining tissue include circulation of heated fluid inside the uterus (either directly or inside a balloon placed in the uterus), laser treatment of the lining, and resistive heating using application of RF energy to the tissue to be ablated. Techniques using RF energy provide an RF electrical signal to one or more electrodes in contact with the subject organ tissue. Electrical current flows from the electrodes and into the organ tissue. The current flow resistively heats the surrounding tissue. Eventually, the heating process destroys the cells surrounding the electrodes and thereby effectuates ablation.

For example, U.S. Pat. No. 5,769,880 (Truckai et al.) and U.S. Pat. No. 6,508,815 (Strul et al.) describe a system for endometrial lining tissue ablation using an electrode carrying member to transmit radiofrequency (RF) energy to cause thermal heating (and, thus ablation) of the tissue, wherein the electrode carrying member is substantially absorbent or permeable to moisture and gases such as steam, and is conformable to the uterine cavity. Suctioning means may additionally be positioned within the electrode carrying member to aid in the removal of moisture, whether gas or liquid, present or generated during the ablation procedure. An array of electrodes is mounted to the surface of the electrode carrying member, and arranged to produce ablation to a predetermined depth. The electrodes may be provided with means for variably controlling ablation depth by changing the electrode density or center to center spacing. Following placement of the ablation device within the patient's uterus, so that the electrodes are in contact with the tissue to be ablated, an RF generator is used to deliver RF energy to the electrodes and to thereby induce current flow from the electrodes to tissue to be ablated. As the current heats the tissue, moisture (such as steam or liquid) leaves the tissue causing the tissue to dehydrate. The moisture permeability or absorbency of the electrode carrying member allows for moisture to leave the ablation site so as to prevent the moisture from providing a path of conductivity for the current. The systems, devices and methods disclosed and described in U.S. Pat. Nos. 5,769,880 and 6,508,815 are well-suited for performing endometrial tissue ablation procedures, e.g., for treating Menorrhagia, the medical term for excessively heavy menstrual bleeding, and are embodied in the NovaSure® endometrial ablation system manufactured and distributed by Hologic, Inc., based in Bedford, Mass. U.S. Pat. Nos. 5,769,880 and 6,508,815 are both hereby fully incorporated by reference.

However, use of the NovaSure endometrial ablation system requires the operator to first measure the length and width of the uterine cavity, and input these dimensions into the controller in order to establish the power level for conducting the endometrial lining ablation procedure. This is because the amount of endometrial lining tissue to be ablated is proportional to the size of the uterine cavity. Additionally, procedure time can vary from as short as approximately one minute in duration, to as long as two minutes in duration, depending on a number of factors e.g., the amount of moisture in the tissue, in addition to the uterine cavity size.

In particular, any RF tissue ablation system must accurately determine the appropriate level of applied power for and during a procedure. This power level must provide sufficient heating to effectuate a complete, (i.e., uniform thickness) ablation. At the same time, however, the power level must be controlled to prevent over-ablation. Moreover, an RF generator must be controlled to respond dynamically to changes in the impedance of the subject tissue.

U.S. Pat. No. 5,954,717 (Behl, et al.) discloses and describes a system and methods for heating solid body tissue (e.g., a tumor) by delivering radio frequency energy through tissue electrodes, wherein the delivered energy is initially controlled to cause an abrupt increase in impedance between the electrodes and the tissue, observed in the form of an abrupt decrease in power delivered to the electrodes. The power at which the impedance increases or the time required to induce such an increase in impedance, are relied upon to determine a desired procedure power level for achieving a maximum sustainable delivery of radio frequency energy to the tissue to achieve complete and uniform heating of the solid tissue volume.

U.S. Pat. No. 6,033,399 (Gines) discloses and describes an electrosurgical generator having an output power control system that employs tissue impedance feedback to cause the impedance of vessel tissue to rise and fall in a cyclic pattern until the tissue is desiccated. The stated advantage of the disclosed power control system is that thermal spread (i.e., non-uniform heating) and tissue-charring (i.e., overheating) are reduced. The output power is applied cyclically by a control system with tissue impedance feedback. The impedance of the tissue follows the cyclic pattern of the output power several times, depending on the state of the tissue, until the tissue becomes fully desiccated. High power is applied to cause the tissue to reach a high impedance, and then the power is reduced to allow the impedance to fall, whereby the delivered thermal energy dissipates during the low power cycle. The control system is said to be adaptive to the tissue in the sense that output power is modulated in response to the impedance of the tissue.

U.S. Pat. No. 6,843,789 (Goble discloses and describes an apparatus for use in performing ablation of organs (such as the uterus), and other tissues, including a radio frequency generator which provides a radio frequency signal to ablation electrodes. The power level of the radio frequency signal is determined based on the subject area of ablation, and is coupled with the ablation electrodes through a transformation circuit. The transformation circuit includes a high impedance transformation circuit, and a low impedance transformation circuit. The high or low impedance transformation circuit is selected based on the impedance of the ablation electrodes in contact with the subject tissue. Vacuum level, impedance level, resistance level, and time are measured during ablation. If these parameters exceed determinable limits the ablation procedure is terminated.

U.S. Pat. No. 6,843,789 (Goble) discloses and describes an electrosurgical system, including an electrosurgical generator and a bipolar electrosurgical instrument, the generator being configured (i.e., programmed) to perform a tissue treatment cycle in which radio frequency energy is delivered to the electrosurgical instrument as an amplitude-modulated radio frequency power signal in the form of a succession of pulses characterized by successive pulses of progressively increasing pulse width and progressively decreasing pulse amplitude. There are periods of at least 100 milliseconds between successive pulses, and the treatment cycle begins with a predetermined pulse mark-to-space ratio. Energy delivery between pulses is substantially zero. Each burst is of sufficiently high power to form vapor bubbles within tissue being treated and the time between successive pulses is sufficiently long to permit condensation of the vapor.

U.S. Pat. No. 8,152,801 (Goldberg, et al.) discloses and describes solid tissue ablation systems and methods, in which radio frequency energy is delivered to the tissue, and a physiological parameter (e.g., impedance or temperature) indicative of a change in moisture concentration of the tissue is sensed. The ablation energy is alternately pulsed on and off to generate an energy pulse train, with the ablation energy being pulsed ON if the sensed physiological parameter crosses a threshold value indicative of an increase in the moisture concentration, and pulsed OFF if the sensed physiological parameter crosses a threshold value indicative of a decrease in the moisture concentration.

U.S. Pat. No. 8,241,275 (Hong et al.) discloses and describes a method of applying ablation energy for transmural tissue wall ablation, e.g., for treating afibrillation, including applying ablation energy at a starting power to a tissue site and monitoring the impedance of the tissue site. Thereafter, the power applied to the tissue site is reduced as a function of a rate of an increase in tissue impedance.

However, none of the foregoing references addresses the specific problems encountered in endometrial lining tissue ablation procedures, for example, accounting for differences in uterine size, or otherwise providing for a uniform and complete endometrial lining ablation in a substantially uniform time period, regardless of differences in uterine cavity size, tissue moisture, or other factors.

SUMMARY

The disclosed embodiments are directed to systems and methods for achieving clinically successful endometrial lining tissue ablations by modulating the delivered power during the procedure in a manner that reaches approximately fifty ohms endometrial lining tissue impedance in approximately two minutes, regardless of the patient's uterine cavity size or other factors, e.g., the patient's monthly cycle, that until now have influenced the procedure power and duration.

In one embodiment, a method of performing an endometrial lining tissue ablation procedure comprises the steps or acts of delivering radiofrequency (RF) power to endometrial lining tissue of a uterine cavity, and modulating the delivered power so that a measured impedance of the endometrial lining tissue tracks a target tissue impedance as a function of time. The target tissue impedance may be derived from a function that approximates a preferred endometrial lining tissue ablation impedance curve, which is based upon a measured impedance of the endometrial lining tissue after RF power has been delivered for a predetermined initial time period, for example, based upon measured impedance data of prior performed ablation procedures. It is preferred that the delivered RF power is substantially constant for the initial time period, and that the initial time period and delivered RF power level are together sufficient such that the measured impedance is representative of the endometrial lining tissue. RF power is preferably thereafter delivered to the endometrial lining tissue until (i) a measured impedance of the endometrial lining tissue reaches predetermined maximum tissue impedance, or (ii) a maximum ablation procedure time is reached, whichever occurs first.

By way of non-limiting example, the preferred endometrial lining tissue ablation impedance curve is based upon an ablation procedure time of approximately 120 seconds and a maximum tissue impedance of approximately 50 ohms, and wherein the function approximating the preferred endometrial lining tissue ablation impedance curve is $I_T = 4 + (49^{(T/120)})$, where $I_T$ is a target tissue impedance (in ohms) for a given time T (in seconds) during the ablation time period.

Modulating the delivered RF power to the endometrial lining tissue includes one of increasing, decreasing, or maintaining constant a delivered RF current at regular power adjustment intervals, wherein at each power adjustment interval, the amperage of the delivered current is not increased or decreased more than a predetermined adjustment limit. By way of non-limiting examples, the predetermined adjustment limit may be in a range of about 2% to about 6%. In one embodiment, the predetermined adjustment limit is 3%. In another embodiment, the predetermined adjustment limit is 5%.

In one embodiment, a method of endometrial lining tissue ablation includes positioning a radiofrequency (RF) applicator within a uterine cavity; delivering an RF current through the applicator to thereby deliver a corresponding RF power to endometrial lining tissue of the uterine cavity; measuring an impedance of the endometrial lining tissue after delivery of the RF power for a predetermined initial time period; and modulating the delivered RF power so that impedance of the endometrial lining tissue tracks a target tissue impedance derived from a function that approximates a preferred endometrial lining tissue ablation impedance curve, based upon the measured impedance of the endometrial lining tissue after RF power has been delivered for the initial time period, wherein RF power is delivered to the endometrial lining tissue until (i) a measured impedance of the endometrial lining tissue reaches a predetermined maximum tissue impedance, or (ii) a predetermined maximum ablation procedure time is reached, whichever occurs first.

In such embodiment, the target tissue impedance $I_t$ for a given time t following the initial time period may be calculated based upon the formula $I_t = I_{max} - ((I_{max} - I_o) * S)$, where $I_{max}$ is a target maximum impedance, $I_o$ is a tissue impedance at time t derived from the function approximating the preferred endometrial lining tissue ablation impedance curve, and S is a scaling factor equal to $(I_{max} - I_{meas})/(I_{max} - I_{to})$, where $I_{meas}$ is the measured impedance of the endometrial lining tissue after RF power has been delivered for the initial time period $t_{initial}$, and $I_{to}$ is a tissue impedance at time $t_{initial}$ derived from the function approximating the preferred endometrial lining tissue ablation impedance curve.

In still another embodiment, an endometrial tissue ablation system includes an RF generator operatively coupled to a controller, wherein the controller is configured to (a) cause the generator to deliver RF power to endometrial lining tissue of a uterine cavity electrically coupled to the generator, and (b) modulate the delivered RF power so that a measured impedance of the endometrial lining tissue tracks a target tissue impedance as a function of time. By way of example, the RF power may be delivered via an applicator including an electrode carrier comprising one or more electrodes thereon configured for being positioned within the uterine cavity for contacting and ablating endometrial lining tissue of the uterine cavity.

The target tissue impedance is preferably derived from a function that approximates a preferred endometrial lining tissue ablation impedance curve, scaled based upon a measured impedance of the endometrial lining tissue after RF power has been delivered for a predetermined initial time period. The controller is preferably configured to cause the RF power to be delivered to the endometrial lining tissue until (i) a measured impedance of the endometrial lining tissue reaches predetermined maximum tissue impedance, or (ii) a maximum ablation procedure time is reached, whichever occurs first.

These and further embodiments and aspects of the disclosed inventions are described herein in detail, in conjunction with the drawings.

BRIEF DESCRIPTION OF THE DRAWINGS

FIG. 2 is a graph illustrating a model target tissue impedance curve for an endometrial tissue lining ablation procedure, assuming an initial tissue impedance of five ohms.

FIG. 5 is a table of discrete tissue impedance values for an endometrial lining tissue ablation procedure derived from a mathematical function that approximates the impedance curve of FIG. 4.

FIG. 7 is a table of discrete tissue impedance values for an endometrial lining tissue ablation procedure derived from a mathematical function that approximates the impedance curve of FIG. 6.

DETAILED DESCRIPTION

Figure 1A:
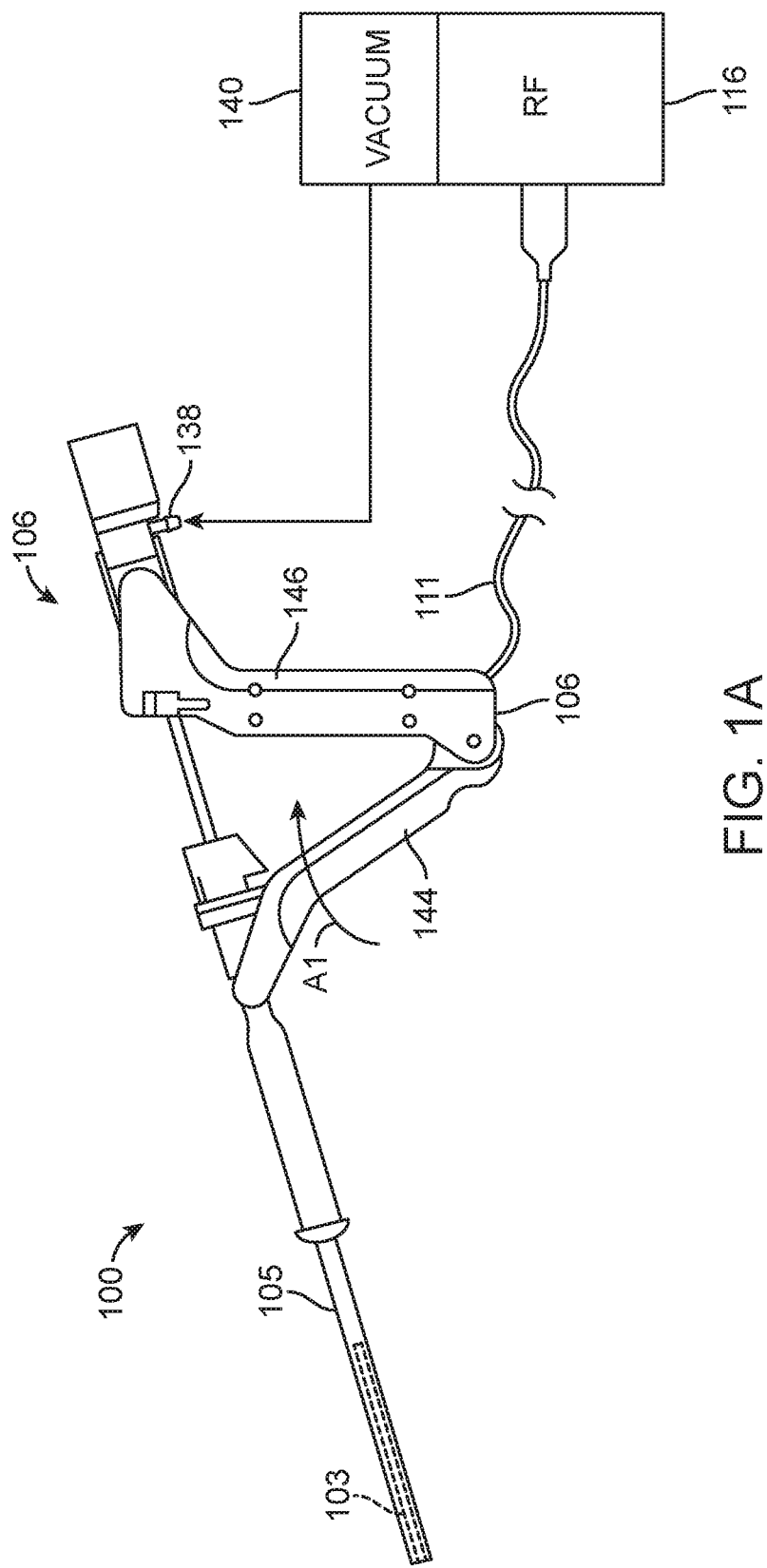
FIG. 1A is a side elevation view of an exemplary prior art RF generator and an ablation device suitable for use with the RF generator, as illustrated and described in above-incorporated U.S. Pat. No. 6,508,815.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of, or as a limitation on the scope of, the disclosed inventions, which are defined only by the appended claims and their equivalents. In addition, an illustrated embodiment of the disclosed inventions needs not have all the aspects or advantages shown, and an aspect or an advantage described in conjunction with a particular embodiment of the disclosed inventions is not necessarily limited to that embodiment and can be practiced in any other embodiments even if not so illustrated.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. All numeric values are herein assumed to be modified by the term "about," whether or not explicitly indicated. The terms "about" and "approximately" generally refer to a range of numbers that one of skill in the art would consider equivalent to the recited value (i.e., having the same function or result). In many instances, the terms "about" and "approximately" may include numbers that are rounded to the nearest significant figure. As used in this specification and the appended claims, numerical ranges include both endpoints and all numbers included within the range. For example, a range of 1 to 5 inches includes, without limitation, 1, 1.5, 2, 2.75, 3, 3.80, 4 and 5 inches.

In accordance with a general aspect of the disclosed inventions, it has been discovered by the present inventors that the duration of an endometrial lining ablation procedure can be tightly controlled by modulating the delivered power during the ablation process. More specifically, the present inventors have reviewed clinical data obtained from a number of endometrial lining ablation procedures, and have determined that a clinically desirable and successful procedure may be achieved by modulating the delivered energy during the course of the procedure in order to reach a target endometrial tissue impedance of approximately fifty ohms over a procedure time period lasting approximately two minutes, regardless of the initial endometrial lining tissue impedance. In particular, if the target tissue impedance is reached in less time, there is a risk that too much energy was delivered too quickly, resulting in possible tissue charring or non-uniform heating of the endometrial lining tissue, both clinically undesirable outcomes. On the other hand, if the target tissue impedance is not reached by the end of a two minute time period, the procedure is taking too long, which is also clinically undesirable.

Thus, it is an object of the disclosed and described embodiments to provide endometrial lining tissue ablation systems and methods of using same for achieving a clinically successful endometrial lining tissue ablation by modulating the delivered power in a manner that reaches a uniform target tissue impedance (e.g., approximately fifty ohms) over a uniform procedure time (e.g., approximately two minutes), regardless of uterine cavity size or other factors (e.g., the patient's monthly cycle) that can influence the amount of power that needs to be delivered for a complete and uniform ablation.

Advantageously, such systems and methods do not require any pre-procedure measuring or input of the uterine cavity size, and allow for a predictable and repeatable ablation procedure time regardless of the uterine cavity size, while maintaining uniform and complete tissue ablation depths.

Exemplary Endometrial Tissue Ablation System

Advantageously, embodiments of the disclosed systems and methods may be software-implemented in an existing or modified controller of the current NovaSure endometrial ablation system, or in a comparable endometrial lining tissue ablation system. As such, to facilitate this detailed description, the NovaSure endometrial ablation system will first be summarily described, with further reference also made to the above-incorporated U.S. Pat. No. 6,508,815. Reference is also made to above-incorporated U.S. Pat. No. 5,769,880. However, it should be appreciated that the inventive concepts disclosed and described herein are not limited to implementation in the NovaSure endometrial ablation system, and may also be employed in other tissue ablation systems.

Figure 1B:
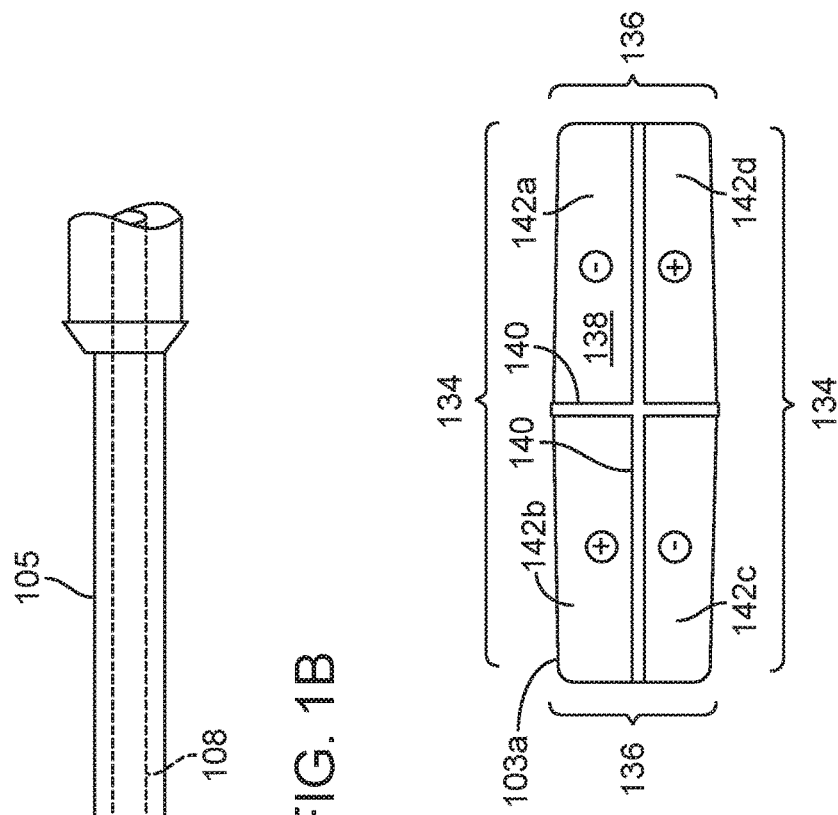
FIG. 1B is a top view of the distal end of the ablation device of FIG. 1A, shown with an applicator head in an extended position.

Referring to FIGS. 1A and 1B, an intrauterine ablation device 100 suitable for use with an RF generator 116 is comprised generally of three major components: an RF applicator head 103, a sheath 105, and a handle 106. The applicator head 103 is slidably disposed within the sheath 105 (FIG. 1A) during insertion of the device into the uterine cavity, and the handle 106 is subsequently manipulated, as indicated by arrow A1, to cause the applicator head 103 to extend from the distal end of the sheath 105 (FIG. 1B). As seen in FIG. 1B, the applicator head 103 extends from the distal end of a length of tubing 108, which is slidably disposed within the sheath 105. The applicator 103 includes an external electrode array 103a and an internal deflecting mechanism 103b used to expand the array for positioning into contact with the tissue.

Figure 1C:
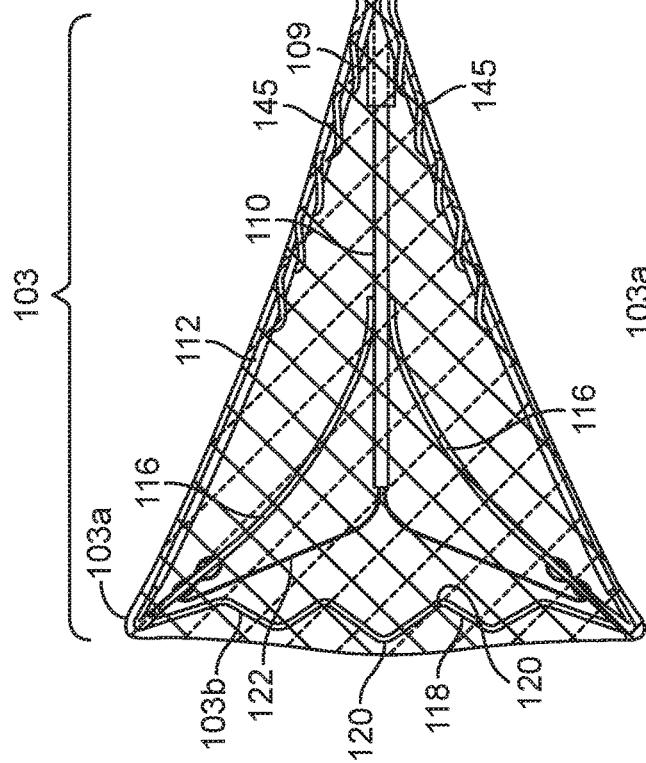
FIG. 1C is a perspective view of the applicator head in the extended position of FIG. 1B.
Figure 1D:
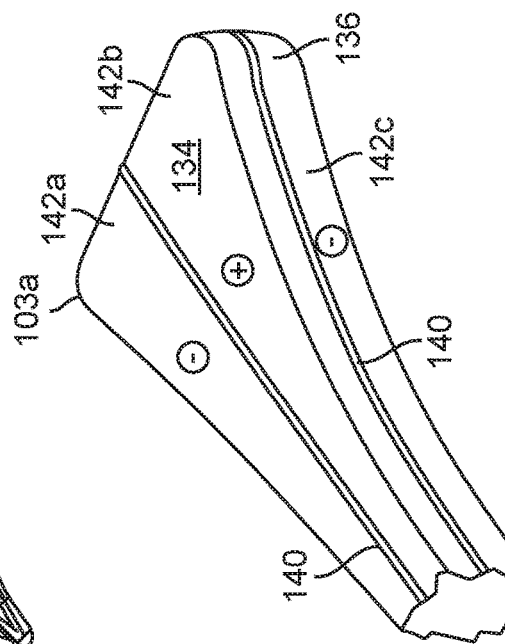
FIG. 1D is a front elevation view of the applicator head in the extended position of FIG. 1B.

The RF electrode array 103a is formed of a stretchable metallized fabric mesh, which is preferably knitted from a nylon and spandex knit plated with gold or other conductive material. Insulating regions 140 (FIGS. 1C, 1D) are formed on the applicator head to divide the mesh into electrode regions. The insulated regions 140 may be formed using etching techniques to remove the conductive metal from the mesh, although alternate methods may also be used, such as by knitting conductive and non-conductive materials together to form the array. The array may be divided by the insulated regions 140 into a variety of electrode configurations. In a preferred configuration shown in FIG. 1C, the insulating regions 140 divide the applicator head into four electrodes 142a-142d by creating two electrodes on each of the broad faces 134. To create this four-electrode pattern, the insulating regions 140 are placed longitudinally along each of the broad faces 134, as well as along the length of each of the faces 136, 138. The electrodes 142a-142d are used for ablation and to measure tissue impedance during use.

The deflecting mechanism 103b and its deployment structure are enclosed within the electrode array 103a. As seen in FIG. 1B, an external hypotube 109 extends from tubing 108, and an internal hypotube 110 is slidably and co-axially disposed within the external hypotube 109. Flexures 112 extend from the tubing 108 on opposite sides of the hypotube 109. A plurality of longitudinally spaced apertures (not shown) may be formed in each flexure 112. During use, these apertures allow moisture to pass through the flexures, and to be drawn into exposed distal end of hypotube 109 using a vacuum source 140 fluidly coupled to the hypotube 109 at vacuum port 138. The internal flexures 116 extend laterally and longitudinally from the exterior surface of hypotube 110, and are each connected to a corresponding one of the flexures 112. A transverse ribbon 118 extends between the distal portions of the internal flexures 116. The transverse ribbon 118 is preferably pre-shaped such that, when in the relaxed condition, the ribbon assumes the corrugated configuration (shown in FIG. 1B), and such that, when in a compressed condition, the ribbon is folded along the plurality of creases 120 that extend along its length.

The deflecting mechanism 103b formed by flexures 112, 116 and ribbon 118 shapes the array 103a into the substantially triangular shape (shown in FIG. 1B), which is particularly adaptable to most uterine shapes. During use, distal and proximal grips 144, 146 forming handle 106 are squeezed towards one another to deploy the array. This action results in relative rearward motion of the hypotube 109, and relative forward motion of the hypotube 110. The relative motion between the hypotubes causes deflection in flexures 112, 116, which thereby deploys and tensions the electrode array 103a.

The flexures 112, 116 and ribbon 118 are preferably made from an insulated spring material such as heat treated 17-7 PH stainless steel. Each flexure 112 preferably includes conductive regions that are electrically coupled to the array for delivery of RF energy to the body tissue. Strands of nylon thread 145 are preferably sewn through the array 103, and around the flexures 112, in order to prevent the conductive regions 132 from slipping out of alignment with the electrodes 142a-142d.

As mentioned above, the RF generator system in the existing NovaSure endometrial ablation system transmits RF ablation power based on the surface area of the target ablation tissue. For uterine ablation, the RF power is calculated using the measured length and width of the uterus. While these measurements may be made using conventional intrauterine measurement devices, the ablation device 100 of the NovaSure endometrial ablation system has been customized to be used to measure the uterine width by transducing the separation of flexures using a mechanical or electrical transducing means. In particular, referring again to FIG. 1B, the ablation device 100 includes non-conductive (e.g. nylon) suturing threads 122 that extend between the hypotube 110 and the distal portion of the deflecting mechanism (FIG. 1B). Threads 122 are connected to an elongate wire (not shown) which extends through the tubing and is coupled to a mechanical transducer such as a rotatable bobbin (not shown) or an electrical transducer such as a strain gauge electrically coupled to an A/D converter to electrically transduce the separation distance of the flexures 112 and to electronically transmit the uterine width to a visual display and/or directly to the RF generator.

Model and Scaled Model Tissue Ablation Impedance Curves

In accordance with a general aspect of the disclosed inventions, the system controller of an endometrial lining tissue ablation system, such as the NovaSure endometrial ablation system, is programmed to monitor the tissue impedance throughout the ablation process, and to modulate (i.e., increase, decrease, or maintain same) the delivered power at regular power adjustment intervals so that the measure tissue impedance tracks a "model" ablation procedure impedance curve, in order to achieved a complete and uniform ablation of the endometrial lining tissue in a standard procedure time, regardless of uterine cavity size, tissue moisture content, or other factors that traditionally vary greatly the procedure power level and duration.

In particular, the present inventors have derived a preferred or "model" target endometrial lining tissue ablation impedance curve, based on historic clinical data, for achieving a clinically complete ablation, as indicated by reaching a tissue impedance of approximately fifty ohms at the end of an ablation procedure lasting approximately two minutes. The model impedance curve is 200 is depicted in FIG. 2, and represents a preferred or "target" endometrial lining tissue impedance (in ohms) 202 as a function of time (t, in seconds) 204, assuming an initial tissue impedance of (or about) five ohms. Notably, the initial tissue impedance is measured after a relatively low level RF energy (55 watts) has been delivered to the endometrial lining tissue for five seconds, in order to reduce the initial moisture content of the uterine cavity and stabilize the tissue so that the measured impedance more accurately represents the tissue impedance rather than excess moisture (e.g., saline) present in the uterine cavity.

Figure 3:
FIG. 3 is a table of discrete target tissue impedance values for an endometrial lining tissue ablation procedure, derived from a mathematical function that approximates the model impedance curve of FIG. 2.

In accordance with a more specific aspect of the disclosed inventions, and with reference to the table 300 shown in FIG. 3, the present inventors have determined a mathematical formula that provides discrete impedance values 302 at one second intervals 304 for the entire two minute ablation procedure, which impedance values approximate the model curve 200 shown in FIG. 2:

$$I_T = 4 + (49^{(T/120)}), \quad (1)$$

where $I_T$ is a target tissue impedance at a given time T (in seconds) of the ablation time period.

By providing target impedance values at precise timing intervals for an entire procedure, the system controller output need only compare the target value (e.g., the values in 302 in table 300) with the actual measured value for each timing interval, and then adjust the delivered power accordingly. This process of adjusting the delivered power at regular timing intervals is referring to herein as modulating the output power, although it may be the case that the power level is not necessarily changed at any given power adjustment interval.

Of course, the model procedure impedance curve 200 shown in FIG. 2 assumes that the initial endometrial lining tissue impedance (i.e., after five seconds of power delivery) will be five ohms; whereas the actual initial impedance may vary significantly from as little as under one ohms, or as much as twelve or more ohms, depending on uterine size (i.e., the amount of endometrial lining tissue to be ablated), tissue moisture content, and other factors. While one approach would be to drive the tissue impedance up or down, as may be the case, as quickly as possible to reach (and thereafter track) the model impedance curve 200, a more preferred approach is to track a scaled impedance curve that generally follows the same trajectory as the model impedance curve 200 and still ends up at approximately 50 ohms after approximately two minutes total procedure time, without risking an incomplete over over-done ablation in an effort to force the procedure to follow curve 200.

Figure 4:
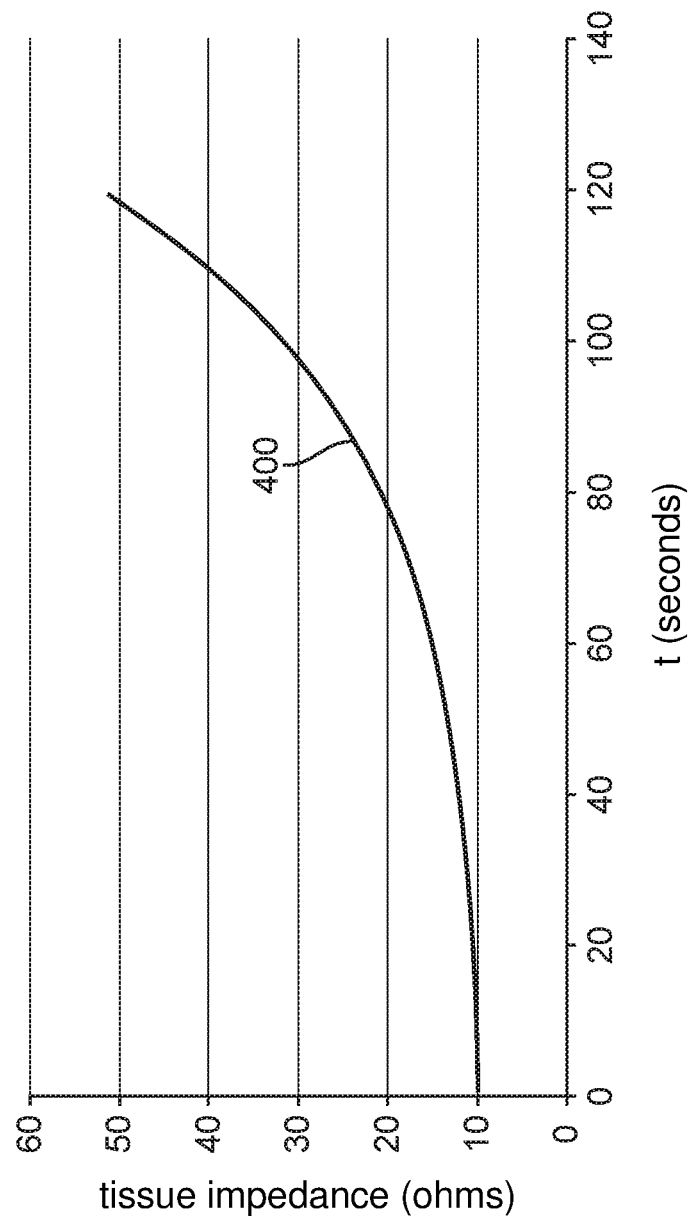
FIG. 4 is a graph illustrating a scaled model target tissue impedance curve for an endometrial tissue lining ablation procedure, assuming an initial tissue impedance of ten ohms.

By way of illustration, a scaled model impedance curve 400 is shown in FIG. 4, which is based upon an initial tissue impedance of (or about) ten ohms after 55 watts RF energy has been delivered to the endometrial lining tissue for five seconds. As with the model impedance curve 200, the scaled model impedance curve 400 represents a target endometrial lining tissue impedance (in ohms) as a function of time (in seconds) for an ablation procedure reaching approximately fifty ohms impedance in approximately two minutes, but starting at ten ohms instead of five ohms.

Figure 6:
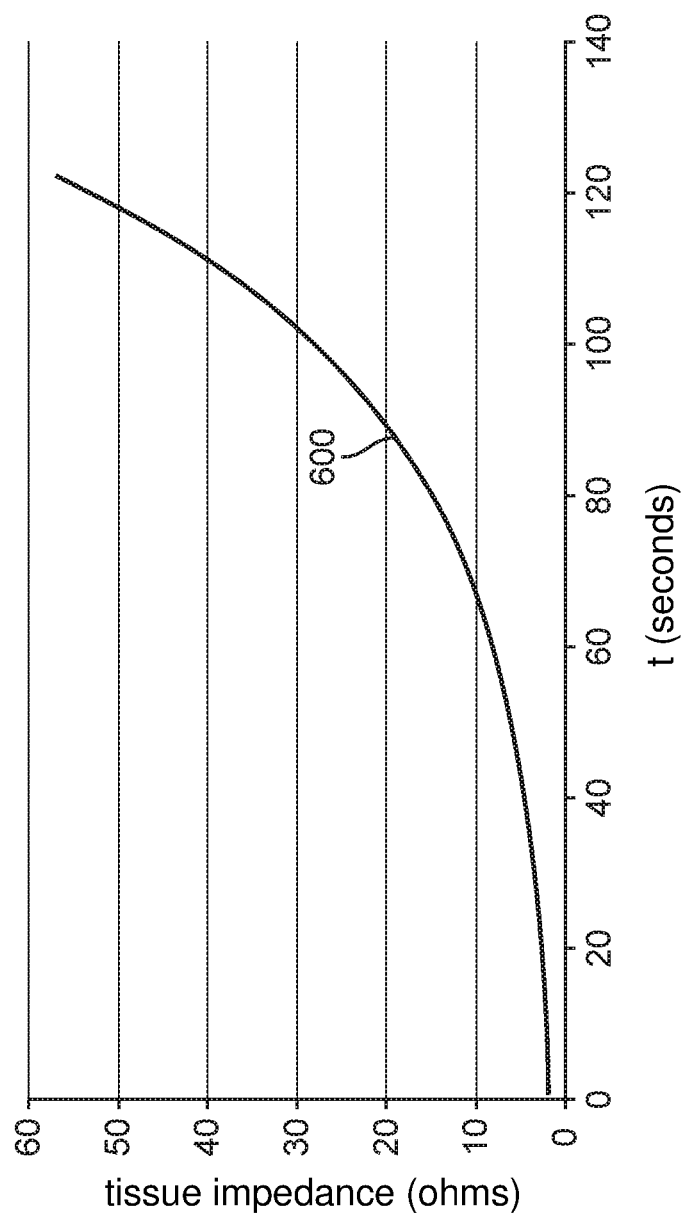
FIG. 6 is a graph illustrating a scaled model target tissue impedance curve for an endometrial tissue lining ablation procedure, assuming an initial tissue impedance of two ohms.
Figure 8:
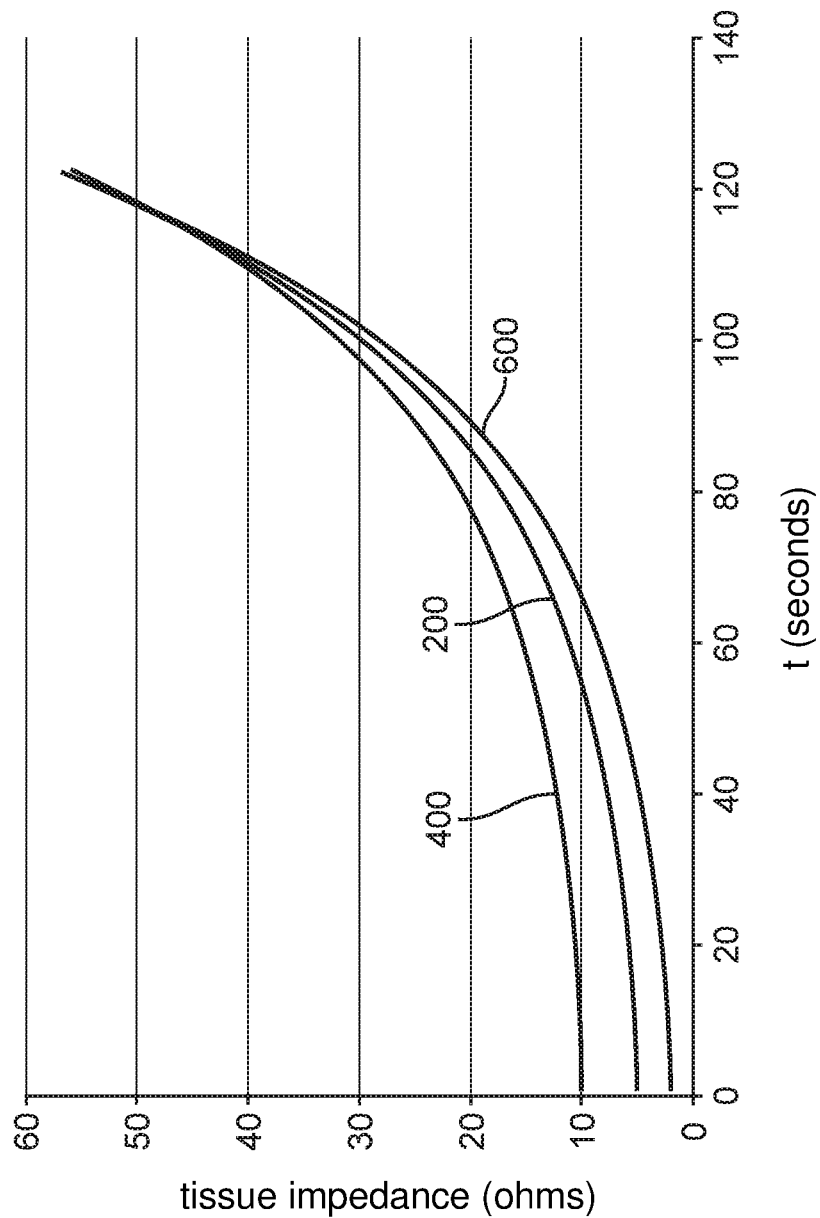
FIG. 8 is a compilation of the tissue impedance curves of FIG. 2, FIG. 4, and FIG. 6, illustrating how each of the curves converges to approximately fifty ohms at around the two minute mark.

By way of further illustration, another scaled model impedance curve 600 is shown in FIG. 6, which is based upon an initial tissue impedance of (or about) two ohms after 55 watts RF energy has been delivered to the endometrial lining tissue for five seconds. As with the model impedance curves 200 and 400, the scaled model impedance curve 600 represents a target endometrial lining tissue impedance (in ohms) as a function of time (in seconds) for an ablation procedure reaching approximately fifty ohms impedance in approximately two minutes, but this time starting at two ohms, instead of five or ten ohms. By way of still further illustration, FIG. 8 is a compilation of the tissue impedance curves 200, 400, 600 of FIGS. 2, 4 and 6, wherein the respective curves converge at approximately fifty ohms at about the two minute mark.

It will be appreciated that, in a preferred implantation, the ablation system controller is preferably programmed using a single formula to determine a set of target impedance values for an ablation procedure based on a given measured initial impedance. Towards this end, and with reference to table 500 shown in FIG. 5, and table 700 shown in FIG. 7, the present inventors have arrived at a further mathematical formula that takes into account the initial measured impedance value, and provides a set of discrete, one second interval target impedance values, $I_t$, that approximate a model impedance curve corresponding to the respective initial measured impedance, as follows:

$$I_t = I_{max} - ((I_{max} - I_o) * S), \quad (2)$$

where $I_t$ is the target tissue impedance (in ohms) for a given time t (in seconds) following the initial power delivery time period, $I_{max}$ is a target maximum tissue impedance, $I_o$ is a tissue impedance at time t derived from the above formula (1) approximating the preferred endometrial lining tissue ablation impedance curve 200, and S is a scaling factor equal to $(I_{max} - I_{meas})/(I_{max} - I_{io})$, where $I_{meas}$ is a measured impedance of the endometrial lining tissue after RF power has been delivered for the initial time period $t_{initial}$, and $I_{io}$ is a tissue impedance at time $t_{initial}$ derived from the function approximating the preferred endometrial lining tissue ablation impedance curve.

Thus, the target impedance values 502 for the respective one second intervals 304 shown in table 500 (FIG. 5) are derived from above formula (2) and approximate the model curve 400 (FIG. 4) for an initial measured tissue impedance of ten ohms. Similarly, the target impedance values 702 for the respective one second intervals 304 shown in table 700 (FIG. 7) are derived from above formula (2) to approximate the model curve 600 (FIG. 6) for an initial measured tissue impedance of two ohms. As can be seen in FIG. 8, the target impedance for all curves 200, 400, 600 converge at approximately fifty ohms at approximately 120 seconds into the procedure.

It will be appreciated by those skilled in the art that the using the above formula (2) to generate a table of discrete target impedance values for a given procedure based on the measured initial impedance is straight forward to implement in a programmable ablation system controller, such as the controller of a NovaSure endometrial ablation system or a comparable tissue ablation system.

Preferably, the delivered RF power is substantially constant for the time period prior to the initial measured impedance from which the target impedance values are derived. However, it is not required to be constant, so long as the initial time period and delivered RF power level are together sufficient such that the initial measured impedance is fairly representative of the endometrial lining tissue. In a presently preferred embodiment, constant power at fifty-five watts is delivered for five seconds prior to obtaining the initial tissue impedance measurement from which the set of target impedance values are derived for the procedure. Thereafter, the delivered power may be decreased, increased, or maintained constant, as appropriate, at each power adjustment interval (discussed below in greater detail), with a minimum delivered power of 20 watts, and a maximum delivered power of 180 watts. The controller may be programmed so that RF power is delivered to the endometrial lining tissue until either (i) the measured impedance of the endometrial lining tissue reaches a predetermined maximum tissue impedance (e.g., fifty ohms), or (2) a maximum procedure time is reached (e.g., two minutes), whichever occurs first.

Thus, in a preferred embodiment, an endometrial tissue ablation system will include an RF generator operatively coupled an RF applicator configured for being positioned within a uterine cavity and for contacting and ablating endometrial lining tissue of the uterine cavity, and a system controller operatively coupled with the RF generator, wherein the controller is configured to (a) cause the generator to deliver an RF current through the one or more applicator electrodes to thereby deliver a corresponding RF power to endometrial lining tissue of a uterine cavity in which the applicator is positioned, and (b) modulate the delivered RF current to thereby modulate the delivered RF power so that a measured impedance of the endometrial lining tissue tracks a target tissue impedance as a function of time, wherein the target tissue impedance is derived from a function that approximates a preferred endometrial lining tissue ablation impedance curve that is based upon a measured impedance of the endometrial lining tissue after RF power has been delivered for a predetermined initial time period. The system continues to deliver RF power to the endometrial lining tissue until the actual tissue impedance reaches a predetermined maximum, or a maximum procedure time is reached, whichever occurs first.

Power Modulation Options

As discussed above, once the ablation system controller has measured the initial endometrial lining tissue impedance and calculated a set of discrete target tissue impedance values for the entire procedure, the controller will thereafter continue to measure the tissue impedance at regular power adjustment intervals, and modulate the delivered power (which corresponds directly to the RF output current), as needed, in order to closely track the respective calculated target tissue impedance values.

The process of modulating output power based on measured tissue impedance is well known in the art of RF ablation controllers. In implementations of the presently disclosed inventions, the power adjustment intervals are preferably no longer than, and more preferably relatively short compared with, the one second target impedance intervals. By way of non-limiting examples, the power adjustment intervals may be each second, 500 milliseconds, 250 milliseconds, 100 milliseconds, or of even less duration. Preferably, the delivered power need not be increased or decreased, as applicable, more than a relatively small percentage difference to maintain tracking of the target impedance value, which changes no more frequently than one second intervals, to avoid possible over-compensation at each adjustment. The absolute amount of a given power adjustment at each interval may be dynamic (e.g., based on the difference between the measured and target impedance values), or static (e.g., a uniform percentage increase or decrease, as applicable. Either way, it is preferred that no one interval adjustment be more than about 3% to about 5% of the current power level.

By way of example, in an exemplary embodiment, an endometrial lining tissue ablation procedure is commenced, and RF current is transmitted to deliver 55 watts power to the endometrial lining tissue for an initial five seconds, at which time an initial tissue impedance measurement is obtained and the corresponding target impedance values for the remaining procedure are calculated using above formula (2). 250 milliseconds later, i.e., 5.25 total seconds into the procedure, the system controller again measures the actual tissue impedance, and compares this measured impedance with the calculated target impedance for t=6 seconds. If the measured tissue impedance is less than the target impedance for t=6 seconds, then the delivered power is increased by up to 3% (i.e., by up to 1.515 watts) to a new delivered power level of up to 56.515 watts. Conversely, if the measured tissue impedance is greater than the target impedance for t=6 seconds, then the delivered power is decreased by no more than 1.515 watts, to a new delivered power level of no less than 53.485 watts. And, of course, if the measured tissue impedance happens to be equal to the target impedance for t=6 seconds, the power level is maintained constant. 250 milliseconds later, i.e., at 5.5 total seconds into the procedure, the process is repeated, and again until the end of the procedure at approximately 120 total seconds. Thus, in this embodiment, there are four power adjustment intervals per second, with a maximum possible increase or decrease of about 12% per second.

In various embodiments, the controller may be programmed to reduce the percentage increase or decrease if the measured impedance for a given power adjustment interval is within close range to the target impedance to avoid overcompensation. Further, in some embodiments the controller may be programmed to not make any adjustments to (i.e., to maintain constant) the current delivered power if the measured impedance is within a certain percentage (e.g., within 1% to 3%) of the target impedance at the end of a given interval. In a presently preferred embodiment, the delivered power is maintained within a range of not less than 20 watts and not greater than 180 watts.

Importantly, the total amount of energy delivered during an endometrial lining tissue ablation using above-described energy is generally optimal, regardless of the uterus size, given the 120 second limit.

Although particular embodiments have been shown and described, it will be understood that they are not intended to limit the present inventions, and it will be obvious to those skilled in the art that various changes and modifications may be made without departing from the scope of the present inventions. The specification and drawings are, accordingly, to be regarded in an illustrative rather than restrictive sense, and the present inventions are intended to cover alternatives, modifications, and equivalents thereof, which may be included within the scope of the present inventions as defined by the claims.

What is claimed is:

1. A system for ablating endometrial lining tissue, comprising:
 a radiofrequency (RF) applicator configured for being positioned within a uterine cavity;

an RF generator electrically coupled to the RF applicator; and a controller operatively coupled to the RF generator, wherein the controller is configured to cause RF power to be delivered from the RF generator to endometrial lining tissue within the uterine cavity via the RF applicator, after the RF power has been delivered for an initial time period, measure an initial impedance of the endometrial lining tissue using an impedance measurement circuit provided by the RF applicator, based upon the measured initial impedance, determine a target impedance of the endometrial lining tissue as a function of time for an endometrial lining ablation procedure, and modulate the RF power delivered to the endometrial lining tissue during the endometrial lining ablation procedure so that an impedance of the endometrial lining tissue tracks the target impedance.

2. The system of claim 1, wherein the controller is configured to determine the target impedance of the endometrial lining tissue for a duration of the endometrial lining ablation procedure based in part upon by scaling a preexisting endometrial lining tissue ablation impedance curve based upon the measured initial impedance of the endometrial lining tissue.

3. The system of claim 1, wherein the controller is configured to determine the target impedance of the endometrial lining tissue for a duration of the endometrial lining ablation procedure based in part upon impedance data obtained from prior performed endometrial lining tissue ablation procedures.

4. The system of claim 1, wherein the RF applicator comprises an electrode carrier including one or more bipolar electrode pairs thereon.

5. The system of claim 1, wherein the controller is configured to cause the RF power to be delivered at a substantially constant power level during the initial time period.

6. The system of claim 5, wherein a duration of the initial time period and the substantially constant power level of the delivered RF power during the initial time period are together sufficient such that the measured initial impedance is representative of an electrical conductivity of the endometrial lining tissue.

7. The system of claim 2, wherein the controller is configured to determine the target impedance of the endometrial lining tissue for the duration of the endometrial lining ablation procedure according to a formula, $I_t = I_{max} - ((I_{max} - I_o) \ast S)$, where $I_t$ is a target tissue impedance for a given time t during the endometrial lining ablation procedure, $I_{max}$ is a target maximum impedance of the endometrial lining tissue, $I_o$ is a projected impedance of the endometrial lining tissue for the given time t during the endometrial lining ablation procedure derived from a function approximating the preexisting endometrial lining tissue ablation impedance curve, and S is a scaling factor equal to $(I_{max} - I_{meas})/(I_{max} - I_{io})$, where $I_{meas}$ is the measured initial impedance of the endometrial lining tissue, $t_{initial}$, and $I_{io}$ is a projected initial impedance of the endometrial lining tissue derived from the function approximating the preexisting endometrial lining tissue ablation impedance curve.

8. The system of claim 7, wherein the duration of the endometrial lining ablation procedure is about 120 seconds, $I_{max}$ is about 50 ohms, and the function approximating the preexisting endometrial lining tissue ablation impedance curve is $I_t = 4 + (49^{(T/120)})$, where T is a given time (in seconds) during the endometrial lining ablation procedure.

9. The system of claim 1, wherein the controller is configured to cause the RF power to be delivered to the endometrial lining tissue until (i) the impedance of the endometrial lining tissue reaches a target maximum tissue impedance, or (ii) a duration of the endometrial lining ablation procedure reaches a target completion time whichever occurs first.

10. The system of claim 1, wherein the controller is configured to modulate the delivery of the RF power to the endometrial lining tissue by causing one of increasing, decreasing, or maintaining constant a delivered RF current to the endometrial lining tissue at regular power adjustment intervals.

11. The system of claim 10, wherein, at each power adjustment interval, an amperage of the delivered RF current is not increased or decreased more than a predetermined adjustment limit.

12. The system of claim 11, wherein the predetermined adjustment limit is about 3%.

13. A system for ablating endometrial lining tissue, comprising:

a radiofrequency (RF) applicator configured to be positioned within a uterine cavity;

an RF generator electrically coupled to the RF applicator; and a controller operatively coupled to the RF generator, wherein the controller is configured to cause RF power to be delivered from the RF generator to the endometrial lining tissue within the uterine cavity via the RF applicator, after the RF power has been delivered for an initial time period, measure an initial impedance of the endometrial lining tissue using an impedance measurement circuit provided by the RF applicator, modulate the delivery of the RF power to the endometrial lining tissue so that impedance of the endometrial lining tissue tracks a target impedance of the endometrial lining tissue as a function of time for a duration of an endometrial lining ablation procedure derived from impedance data obtained from prior performed endometrial lining tissue ablation procedures, and cease delivery of the RF power to the endometrial lining tissue when (i) the impedance of the endometrial lining tissue reaches a target maximum tissue impedance, or (ii) the duration of the endometrial lining ablation procedure reaches a target completion time, whichever occurs first.

14. The system of claim 13, wherein the controller is configured to modulate the delivery of the RF power to the endometrial lining tissue by causing one of increasing, decreasing, or maintaining constant a delivered RF current to the endometrial lining tissue at regular power adjustment intervals, wherein, at each power adjustment interval, an amperage of the delivered RF current is not increased or decreased more than a predetermined adjustment limit.

15. The system of claim 13, wherein the controller is configured to determine the target impedance of the endometrial lining tissue for the duration of the endometrial lining ablation procedure according to a formula, $I_t = I_{max} - ((I_{max} - I_o) \ast S)$, where $I_t$ is a target tissue impedance for a given time t during the endometrial lining ablation procedure, $I_{max}$ is a target maximum impedance of the endometrial lining tissue, $I_o$ is a projected impedance of the endometrial lining tissue for the given time t during the endometrial lining ablation procedure derived from a function approximating a preexisting endometrial lining tissue ablation impedance curve, and S is a scaling factor equal to $(I_{max}-I_{meas})/(I_{max}-I_{io})$, where $I_{meas}$ is the measured initial impedance of the endometrial lining tissue, and $I_{io}$ is a projected initial impedance of the endometrial lining tissue derived from the function approximating the preexisting endometrial lining tissue ablation impedance curve.

16. The system of claim 15, wherein the duration of the endometrial lining ablation procedure is about 120 seconds, $I_{max}$ is about 50 ohms, and the function approximating the preexisting endometrial lining tissue ablation impedance curve is $I_t=4+(49^{(T/120)})$, where T is a given time (in seconds) during the endometrial lining ablation procedure.

\* \* \* \* \*